United States Patent [19]
Bunge

[11] 4,017,191
[45] Apr. 12, 1977

[54] TWO-BEAM PHOTOMETER WITH ROTATABLE GRADED INTERFERENCE FILTER

[75] Inventor: Konrad Bunge, Cologne, Germany
[73] Assignee: Bayer Aktiengesellschaft, Leverkusen, Germany
[22] Filed: June 20, 1975
[21] Appl. No.: 588,750
[30] Foreign Application Priority Data
   June 22, 1974 Germany .......................... 2430011
[52] U.S. Cl. .............................. 356/188; 356/205; 356/229
[51] Int. Cl.² ...................... G01J 3/50; G01N 21/24
[58] Field of Search ............. 350/166; 356/51, 188, 356/189, 201, 204, 205, 229; 250/343

[56] References Cited
   UNITED STATES PATENTS
   3,811,781  5/1974  Lowy .................................. 356/188

Primary Examiner—John K. Corbin
Assistant Examiner—F. L. Evans
Attorney, Agent, or Firm—Burgess, Dinklage & Sprung

[57] ABSTRACT

The two-beam photometer is suitable for extinction measurement on weakly-absorbent samples. The principle of measurement is based on a wavelength selection in either the comparison beam and the measuring beam. In the beam configuration measuring and comparison beam are coincident in space and follow each other periodically. The wavelength ranges in measuring beam and comparison beam is selected by a graded interference filter which is arranged perpendicular to the optical axis and rotatable about this axis. In the zone of the graded interference filter the path of the beam is formed by two narrowly limited beams symmetrically to the optical axis. Both beams are produced preferably by two light sources whose distance may be varied in a direction perpendicular to the optical axis while the symmetry with respect to the optical axis is maintained.

6 Claims, 8 Drawing Figures

TWO-BEAM PHOTOMETER WITH ROTATABLE GRADED INTERFERENCE FILTER

This invention relates to a two-beam photometer comprising an arrangement for selecting a range of wavelengths for the path of the measuring beam and another range for the path of the comparison beam. The path of the measuring beam and the path of the comparison beam coincide in space but follow each other periodically in time. Photometers of this kind are particularly suitable for extinction measurements on weakly-absorbent samples which absorb selectively at a particular wavelength.

The principle of measuring the concentration of a sample by determining its optical absorption or transparency is already known in the field of measuring techniques. FIG. 1, for example, shows the transmission T of a sample measured by a conventional two-beam photometer plotted as a function of the wavelength $\lambda$. The sample is assumed in this case to be pure, that is to say free from any interfering substances which would cause additional absorption. In that case, the transmission value T0 measured at $\lambda 0$ is already a measure of the concentration which is required to be determined. More difficult is the determination of the concentration of a sample if an additional absorbing substance is present as a so-called interference substance. FIG. 2, for example, shows a spectrum recorded by means of a photometer in such a case. The interfering absorption produced by a foreign substance manifests itself by a decrease in the transparency in the direction of longer wavelengths. Such a recording curve may be interpreted, for example, as follows: Perpendiculars are drawn from the axis at the points P0 ($\lambda 0$, 0), P1 ($\lambda 1$, 0) and P2 ($\lambda 2$, 0) to intersect the transmission curve at Q0. The straight line P0, Q0, etc. is projected to intersect the straight line $\overline{Q1, Q2}$, at Q 12. The ratio of the distance $\overline{P0, Q0}$ to $\overline{P0, Q}$ 12 is then a measure of the required concentration. This method has proved to be successful as a laboratory method of measurement but its application to industrial measuring techniques gives rise to difficulties, for example if the photometer is to be used for the direct monitoring of process streams in the chemical industry. The reasons for these difficulties are said to lie in the low speed of scanning when recording the spectrum and the large amount of time consumed for interpreting the transmission curve. Moreover, conventional commercial two-beam photometers are large and cumbersome apparatus not suitable for use as industrial measuring devices. The elements used for dispersing the light are optical grids or prisms which transmit the whole range of wavelengths.

It is an object of this invention to provide a two-beam photometer which is sturdy and simple in construction and can be used in the chemical industry for monitoring process streams. The sensitivity of the photometer should be high enough to enable it to determine concentrations even of very weakly-absorbing substances. Determination of the concentration should still be possible if the sample under investigation contains interfering foreign substances which also absorb strongly in the absorption region of the substance under investigation.

According to the invention there is provided a two-beam photometer comprising an arrangement for selecting a range of wavelengths for the path of measuring beam and another range of wavelengths for the path of a comparison beam, the path of the measuring beam and the comparison beam coinciding in space but following each other periodically in time, wherein the arrangement for selecting the wavelength ranges comprises a graded interference filter which is perpendicular to an optical axis and rotatable about the optical axis, and in the zone of the graded interference filter the path of the beam is formed by two narrowly limited (as defined herein) beams situated symmetrically on either side of the optical axis.

By "narrowly limited" is meant that the diameter of the beam of light be sufficiently small that the wavelength resolution of the graded interference filter is not limited by the diameter of the beam. The maximum permissible diameter can very easily be determined experimentally. In practice, beams with diameters of from 2 to 3 millimeters are usually employed.

The photometer is preferably equipped with two sources of light whose distance from each other perpendicular to the optical axis is variable, while the symmetry with respect to the optical axis is maintained. When this distance is altered, the distance between beams incident on the filter changes accordingly. The range of wavelengths over which the interference filter sweeps is thereby reduced or increased.

The principle of measurement based on a rotating graded interference filter enables a very simple and compact construction of photometer to be used. One particular advantage of this method is the ease with which the range of wavelengths can be adjusted to the given analytical conditions. The apparatus can therefore easily be optimised for each individual case. The absorption of foreign substances near the point of absorption of the substance under investigation does not interfere with the measurement if the quantity used for measurement is the ratio of the amplitude DS to the mean valve $\overline{S}$ of the signal received by the photoelectric receiver (see FIG. 6).

It can be shown that the results obtained by this method approximately correspond to the results obtained with the graph of FIG. 2 (as described above), provided that the absorption of the interfering substances is not selective in the absorption region $\lambda 0$, that is to say the interfering substances must not have a pronounced absorption band in this region.

The invention will now be described in more detail with reference to an example illustrated in the drawing in which FIG. 1 shows the transmission curve of an absorbing substance free from interfering substances;

Figure 1:
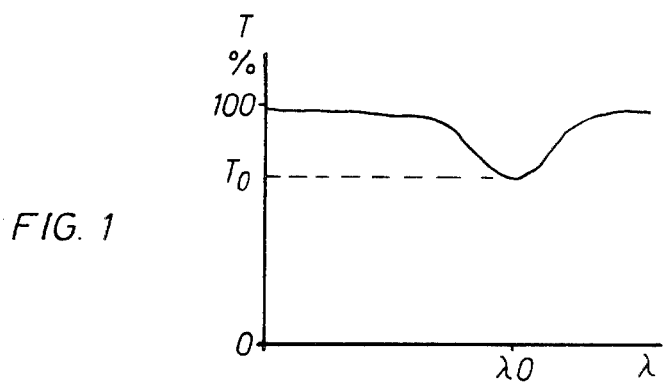
Figure 2:
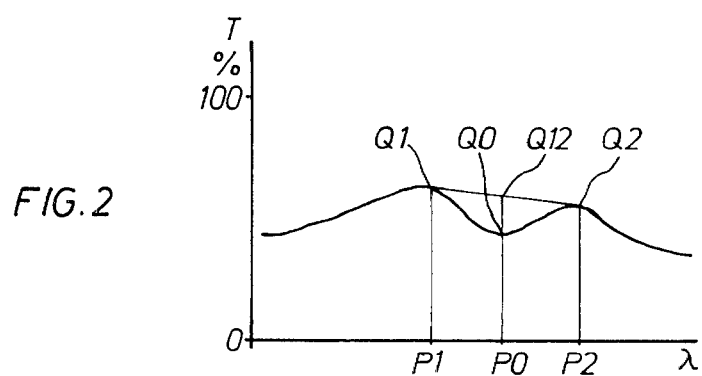
FIG. 2 shows the transmission curve of the substance in the presence of an interfering substance which absorbs in the same region.
Figure 5A:
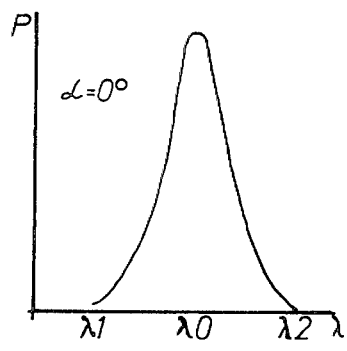
Figure 5B:
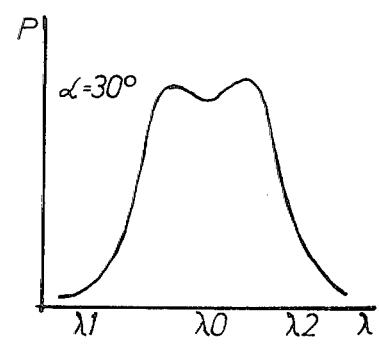
Figure 5C:
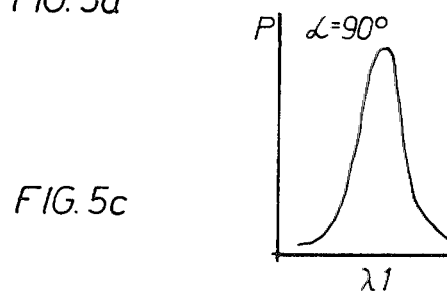
Figure 6:
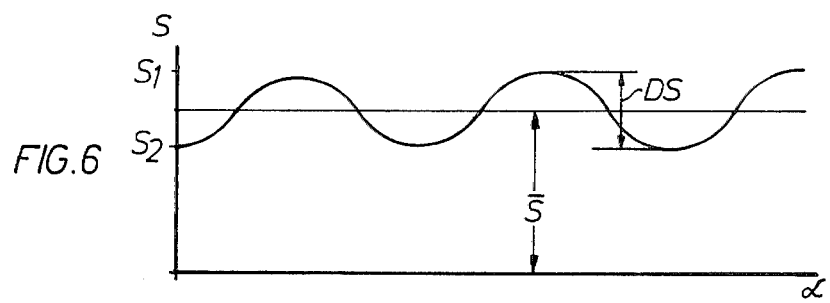

FIGS. 5a – c represent the spectral range transmitted by the interference filter at various points in time during a measuring period;

FIG. 6 represents the signal recorded at the output of the photometer as a function of time or of the angle of rotation $\lambda$ of the interference filter and FIGS. 1 and 2 were already explained in the introductory part of the description in which the principle of measurement was described.

Figure 3:
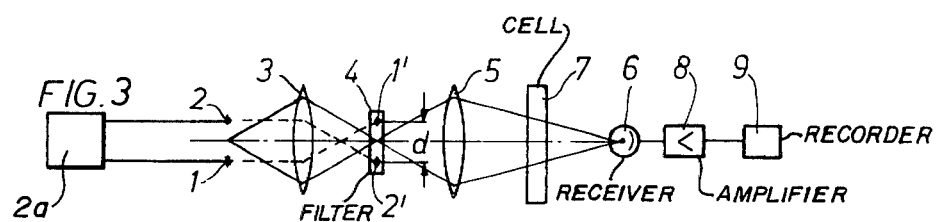
FIG. 3 shows the path of light through the photometer.

FIG. 3 shows the path of the beam of light and the essential elements of the two-beam photometer. Light beams from two sources of light 1 and 2, e.g. incandescent lamps, pass through a lens 3 to be focused on a graded interference filter 4 where they produce images 1' and 2'. In other words, lens 3 produces two beams of light each corresponding to one of the light sources 1 and 2, the diameters of which beams in the region of the interference filter 4 are equal to the diameters of the images 1' and 2'. The beams passing through the interference filter are then focused on a photoelectric receiver 6 by a lens 5. A cell 7 containing the sample to be investigated is situated between the photoelectric receiver or converter 6 and the lens 5. Absorption of light in its passage through the cell 7 then results in weakening of the electric signal transmitted by the photoelectric converter 6. This signal is amplified by an amplifier 8 and then recorded in its relation to time by a recording instrument 9. The most important part of the whole arrangement is the graded interference filter 4. It is arranged to be rotatable about the optical axis, and when the photometer is in operation it rotates at a frequency of about 50 Hz. It may be driven, for example, by a synchronous motor (not shown). The interference filter 4 may in addition be displaced perpendicularly to the optical axis in the direction of its change of wavelength. For this purpose, the interference filter 4 is mounted together with a drive on a carriage which is connected to a fine motion drive. Thus, filter 4 is outfitted with means 4a for displacing the filter perpendicularly with respect to the optical axis in the direction of its change of wavelength.

Figure 4:
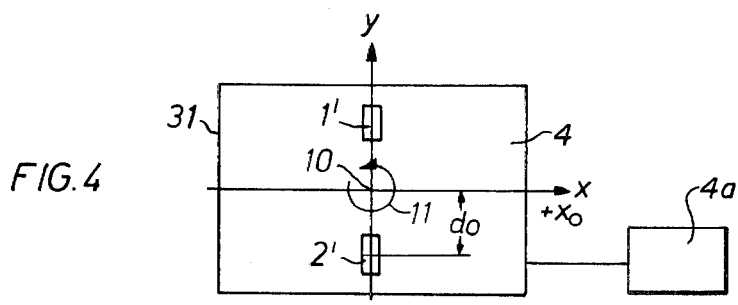
FIG. 4 illustrates the mode of operation of the graded interference filter.

The mode of operation of the graded interference filter 4 will now be explained with reference to FIGS. 4 and 5. FIG. 4 shows a section through the optical arrangement of FIG. 3 at the interference filter 4. The optical axis passes through the filter 4 at point 10 which is taken as the origin of a coordinate system with axes X and Y. The filter is in the form of a rectangle with edges $2 X_o$ and $2 Y_o$. The filter is arranged in such a position in FIG. 4 that the wavelengths to which it is maximally permeable increase or decrease continuously from left to right. Each straight line parallel to the Y axis which represents X = const. corresponds to a certain wavelength to which the filter is permeable. The shortest wavelength capable of passing through the filter, for example, lies at $X = -X_o$ and the longest at $X = +X_o$. If, therefore, the filter is illuminated with a slit of white light parallel to the Y-axis while the filter is moved from left to right through the beam of light, then the colour of light transmitted by the filter changes continuously from $\lambda(-X_o)$ to $\lambda(+X_o)$.

Graded interference filters of this kind have recently become available commercially and are sold, for example, by Schott (Mainz) under the tradename VERIL IB 200. One such filter, for example, measures about 15 cm in the direction of variable wavelengths (X-direction in FIG. 4) and about 2.5 cm perpendicularly thereto (Y-direction in FIG. 4). A portion measuring 3 cm in the direction of variable wavelengths is then selected from this filter to produce a rectangular filter measuring 3 × 2.5 cm. This filter may, for example, cover wavelengths ranging from 1800 to 2000 nm and the width of the band spanning the wavelengths which are transmitted at half maximum intensity is about 100 nm. The axis of rotation lies at the point of intersection of the diagonals of the rectangle.

The images 1', 2' of the incandescent filaments 1 and 2 projected by the optical system 3 are also indicated in FIG. 4.

The size of the images and hence also the diameter of the partial beams of light incident on the interference filter 4 may be 2 × 2 mm, for example. The centres of the images 1' and 2' may be situated, for example each 10 mm from the axis. If this filter is rotated continuously about the optical axis (perpendicular to the plane of the paper in FIG. 4), the transmission of wavelengths in the region of 1900 nm is followed by the transmission of a combination of wavelengths in the regions of about 1966 nm and 1834 nm. The width of the band of transmitted light is substantially equal to the given width at half maximum intensity for the filter, which is 100 nm. In this case, therefore, the width of the band transmitted is practically unaffected by the size of the images 1' and 2'. It is only if substantially larger areas of light, corresponding to a larger diameter of beams of light were projected as images that the width at half maximum intensity would also increase.

If one wished to keep the mean wavelength of the range of light transmitted by the filter unchanged (at 1900 nm) but to restrict the bands of transmitted light on either side of the mean value to 1850 nm and 1950 nm, the centres of the images 1', 2' on the graded interference filter would have to be arranged at a distance of 7.5 mm from the centre of rotation. If one wished to alter the mean wavelength, the interference filter would have to be shifted in the direction of the X-axis towards shorter or longer transmitted wavelengths.

According to FIG. 3, the images 1' and 2' and the corresponding beams of light are produced by two independent light sources 1 and 2. The light currents of the partial beams are generally adjusted to each other, for example by suitably adjusting the voltage supply of one or both of the independent incandescent lamps 1 and 2 or by reducing the optical power of one or both of the beams. The lamps 1 and 2 are mounted on an optical bench so that their distance from the optical axis can be adjusted, but always in such a way that their positions remain symmetrical with respect to the optical axis. Thus, means 2a are provided for varying the distance of the beam from the optical axis while maintaining the beams symetrical with respect to the optical axis. When this distance is adjusted, the position of the images 1' and 2' on the interference filter 4 and hence the position of the bands of wavelengths on either side of the mean wavelengths change accordingly. Instead of using two independent sources of light one could, of course, use a single source of light in combination with a double aperture diaphragm. In that case, the distance of the two apertures would have to be symmetrically adjustable with respect to the optical axis. The spectral light intensity P behind the interference filter 4 when white light is used as source of illumination will now be investigated in more detail with reference to FIG. 3. In FIGS. 5a and 5c, the permeability of the interference filter 4 is represented graphically as a function of the wavelengths at three different angular positions of the filter ($\alpha=0, \alpha= 30°, \alpha= 90°$). In the position $\alpha = 0$, the images 1' and 2' are situated one above the other, as represented in FIG. 4. The filter then transmits a wavelength $\lambda 0$ (or more accurately a range of wavelengths around $\lambda 0$) since the graded interference filter 4 is illuminated only along the straight line X = 0 (see FIG. 4). In the position $\alpha= 90°$, on the other hand, the images 1' and 2' are situated at $X = +d_o$ and $X = -d_o$. In this position, the filter transmits two wavelengths $\lambda 1$ and $\lambda 2$ corresponding to the two zones $X =+d_o$ and $X =$ $-d_o$ on the interference filter. In the course of the rotation of the filter from $\alpha=0$ to $\alpha=90°$, the spectral distribution continuously changes from substantially monochromatic light (FIG. 5a) to substantially bichromatic light (FIG. 5c). In between these two end points, the spectral distribution passes through transitional areas as represented, for example, for $\alpha=30°$ in FIG. 5b. When the filter is rotated continuously, it passes twice through the wavelength distribution shown in FIG. 5a and twice through the distribution shown in FIG. 5c during each period of rotation. This modulation of wavelengths forms the foundation of the two-beam photometer described here in which the measuring beam and comparison beam follow each other in time. The wavelength of the measuring beam lies in the absorption region $\lambda 0$ of the substance which is to be investigated. The comparison beam contains the two wavelengths $\lambda 1$ and $\lambda 2$ which lie outside the absorption region $\lambda 0$.

The light in which the wavelengths have been modulated by the interference filter 4 passes through the cell 7 filled with a gaseous or liquid sample to produce and electric signal in the photoelectric converter 6. This signal is amplified by a wide band direct voltage amplifier 8 and plotted against time by the recording instrument 9. FIG. 6 shows a record obtained in this way. plotting the resulting signal against time is equivalent to plotting it as a function of the angle of rotation $\alpha$. The electric signal measured is composed of an alternating voltage of amplitude DS/2 and a direct current component $\overline{S}$. The ratio of the amplitude DS of the signal to its mean value $\overline{S}$ is a measure of the concentration of the substance under investigation. This can be understood with reference to FIG. 2. The graduated light transmission of the interference filter is adapted to the absorption of the sample under investigation so that $\lambda 1$, $\lambda 0$ and $\lambda 2$ coincide with the points P1, P0 and P2. Light of wavelength $\lambda 1$ and $\lambda 2$ (angle of rotation $\alpha=90°$, see FIG. 5c) then produces a signal in the receiver which is proportional to the mean value of the two transparencies $$\frac{\overrightarrow{Q1, P1} + \overrightarrow{Q2, P2}}{2} = \overrightarrow{Q12, P0}.$$

The sample mixed with interfering substance is maximally transparent to $\lambda 1$ and $\lambda 2$. The electric signal produced passes through the maximum values shown in FIG. 6.

The minimum values in FIG. 6 correspond to the wavelength $\lambda 0$ at which the sample + interfering substance is least transparent (see FIG. 2). In this case, the transparency has the value $\overrightarrow{P0, Q0}$. In the explanation of FIG. 2 given above, it was already pointed out that the ratio of $\overrightarrow{P0, Q0}$ to $\overrightarrow{P0, Q12}$ is approximately proportional to the concentration which is required to be determined. The principle of measurement on which the new two-beam photometer is based therefore enables the concentration to be determined directly from the recorded signal. The formation of ratio is carried out, for example, electronically by means of a division circuit. Instead of a linear amplifier 8, a variable amplifier may be used in which the amplification automatically adjusts itself so that the mean value $\overline{S}$ remains constant. The amplitude DS can in that case be used directly as the measured value. Interpretation of the result is in this case particularly simple. The correlation described above between the concentration of the sample to be measured and the output signal on the photometer is only an approximation. For wide ranges of concentration, the photometer must in all cases be calibrated empirically.

In the description of FIG. 3, it was mentioned that the power of the beams corresponding to the images 1', 2' are generally arranged to be equal. In some cases, however, it may be advantageous to use differing powers, in particular so that the power of one of the two beams, say beam 2' is reduced to zero. This case may arise, for example, if only those wavelengths lying on one side of the measuring wavelength may or can be used. This variation does not depart from the basic principle of measurement with the photometer but the method of interpretation described with reference to FIGS. 1 and 2 must be slightly modified.

The advantages of the two-beam photometer according to the invention are summarised below:

1. The new principle of measurement enables a simple and compact construction of apparatus to be obtained so that the photometer can be used for the continuous automatic analysis of gaseous or liquid process streams.

2. The wavelength $\lambda 0$ at which the apparatus is required to be operated can easily be varied within certain limits simply by slightly shifting the graded interference filter 4 along the X-axis (see FIG. 4). This change in the measuring wavelength is particularly important because in many cases one can only find the optimum wavelength for measurement in the course of operation.

3. The difference between the two comparison wavelengths $\lambda 2$ and $\lambda 2$ can also be selected as desired within a certain range, simply by adjusting the images 1' and 2' in the direction of the Y-axis or adjusting the distance between the light sources 1 and 2.

4. With these photometers, different examples of one type of apparatus can easily be adjusted so that the same measured values are obtained for the same material to be measured. This is possible even if the interference filters used in the different examples differ considerably from each other in their spectral properties.

5. Any variation of temperature has practically the same effect on the measuring wavelength and on the comparison wavelengths. As a first approximation, therefore, the measured values obtained are unaffected by temperature.

6. The transition from measuring wavelength to comparison wavelengths produces no sudden change in signal. In the previously used two-beam photometers with filters, the change from measuring beam to comparison beam produces sudden changes which are liable to cause trouble.

What we claim is:

1. A two beam photometer comprising:
   a. means for providing two light beams to provide a measuring beam and a comparison beam,
   b. a first lens for receiving said beams and directing them in the direction of the optical axis of the lens,
   c. a graded interference filter perpendicular to the optical axis and rotatable about the optical axis, disposed on the optical axis for receiving the beams from the first lens, for selecting a range of wavelengths for the measuring beam and another range of wavelengths for the comparison beam, the paths of the beams in the zone of the filter being narrowly limited and situated symmetrically on either side of the optical axis,
d. the path of the measuring beam and the comparison beam coinciding in space but following each other periodically in time,
e. a second lens for receiving the beams from the filter and directing them further along the optical axis,
f. a cell for holding a specimen to be investigated disposed in the path of beams from the second lens for at least partial transmission of the beams through the specimen,
g. a photoelectric means for receiving the beams passing through the specimen, and
h. means operatively connected to the photoelectric means for recording the output of the photoelectric means.

2. A two beam photometer as claimed in claim 1, wherein means (a) comprises means for varying the distance of the beams from the optical axis while maintaining the beams symmetrical with respect to the optical axis.

3. A two beam photometer as claimed in claim 1, and means for displacing the filter perpendicularly with respect to the optical axis in the direction of its change of wavelength.

4. A two beam photometer as claimed in claim 2, and means for displacing the filter perpendicularly with respect to the optical axis in the direction of its change of wavelength.

5. A two-beam photometer comprising:
a. source means for projecting two beams of light which are symmetrically located with respect to an optical axis;
b. a graded interference filter positioned perpendicular to said optical axis and in the path of said two beams and being rotatable about said optical axis to produce a range of wavelengths for a measuring beam and a range of wavelengths for a comparison beam, the areas of the said beams in the zone of the filter being narrowly limited;
c. cell means for holding a specimen to be investigated disposed in the path of said measuring and comparison beams for at least partial transmission of the beams through the specimen;
d. said comparison and measuring beams traversing the same path through the specimen;
e. and receiving means receiving the beams passing through the specimen for converting said beams into information signals.

6. A two-beam photometer as in claim 5, in which said optical axis intersects said filter at a point midway between the upper and lower edges of said filter.

* * * * *

UNITED STATES PATENT AND TRADEMARK OFFICE
CERTIFICATE OF CORRECTION

PATENT NO. : 4,017,191
DATED : April 17, 1977
INVENTOR(S) : Konrad Bunge

It is certified that error appears in the above–identified patent and that said Letters Patent are hereby corrected as shown below:

Column 2, line 12, after "light" insert --must--.

Column 4, line 56, change "5a and 5c" to --5a to 5c--.

Column 6, line 35, change "$\lambda 2$ and $\lambda 2$" to --$\lambda 1$ and $\lambda 2$--.

Signed and Sealed this twelfth Day of July 1977

[SEAL]

Attest:

RUTH C. MASON
Attesting Officer

C. MARSHALL DANN
Commissioner of Patents and Trademarks